United States Patent [19]

Francis

[11] 4,044,983
[45] Aug. 30, 1977

[54] RETRACTABLE PLASMA CONTAINER HOLDER

[75] Inventor: Orville Francis, Piqua, Ohio

[73] Assignee: Indian Head, Inc., New York, N.Y.

[21] Appl. No.: 635,419

[22] Filed: Nov. 26, 1975

[51] Int. Cl.² ............................................. A47F 5/00
[52] U.S. Cl. ................................. 248/293; 248/294; 248/311.3; 248/318
[58] Field of Search ............... 24/31 V, DIG. 18; 222/181; 248/95, 289, 290, 291, 293, 294, 302, 303, 317, 318, 320, 321, 322, 323, 324, 327, 339, 340, 341, 311.3

[56] References Cited

U.S. PATENT DOCUMENTS

| 235,129 | 12/1880 | Coulter | 248/200 |
|---|---|---|---|
| 285,094 | 9/1883 | Wode | 248/294 |
| 1,020,791 | 3/1912 | Baldwin | 248/303 |
| 1,289,830 | 12/1918 | Leimecke | 211/12 |
| 1,584,722 | 5/1926 | Bohmbach | 248/293 |
| 2,253,444 | 8/1941 | Muller | 248/95 X |
| 2,349,054 | 5/1944 | Phipps | 248/106 |
| 2,684,226 | 7/1954 | Sundell et al. | 248/294 |
| 2,711,300 | 6/1955 | Nelson | 248/291 X |
| 2,791,392 | 5/1957 | Black | 248/293 |
| 2,936,992 | 5/1960 | Browning | 248/313 UX |
| 3,230,954 | 1/1966 | Burgess et al. | 128/214 |
| 3,313,511 | 4/1967 | Koerner et al. | 24/DIG. 18 |
| 3,337,880 | 8/1967 | Florek | 5/92 |
| 3,386,589 | 6/1968 | Prete | 211/118 |
| 3,395,882 | 8/1968 | Marshall | 248/318 |
| 3,782,672 | 1/1974 | Larson | 248/302 |
| 3,923,279 | 12/1975 | Gresley et al. | 248/318 |
| 4,005,844 | 2/1977 | Richmond | 248/311.3 |

FOREIGN PATENT DOCUMENTS

| 45,760 | 7/1909 | Switzerland | 248/294 |
|---|---|---|---|
| 14,866 | 11/1897 | Switzerland | 248/290 |
| 18,298 | 8/1903 | United Kingdom | 248/290 |

Primary Examiner—Lawrence J. Staab
Attorney, Agent, or Firm—Brumbaugh, Graves, Donohue & Raymond

[57] ABSTRACT

A holder for a plasma container has a bracket designed to be fastened to the ceiling of an ambulance. The bracket comprises a ceiling plate having an elongated slot, a support prism extending across the slot, and spring clip means resiliently urging the prism against the plate for holding a flat face of the prism against the plate but permitting a substantial force to rotate the prism to another face. A hanger extends from the prism through the slot so that, in one position of the prism, it is held parallel to the ceiling and out of the way, but, by merely rotating the prism, it is held normal to the ceiling for receiving a plasma container. A hook and loop cloth strap extends about the hanger for holding the container on the hanger.

14 Claims, 2 Drawing Figures

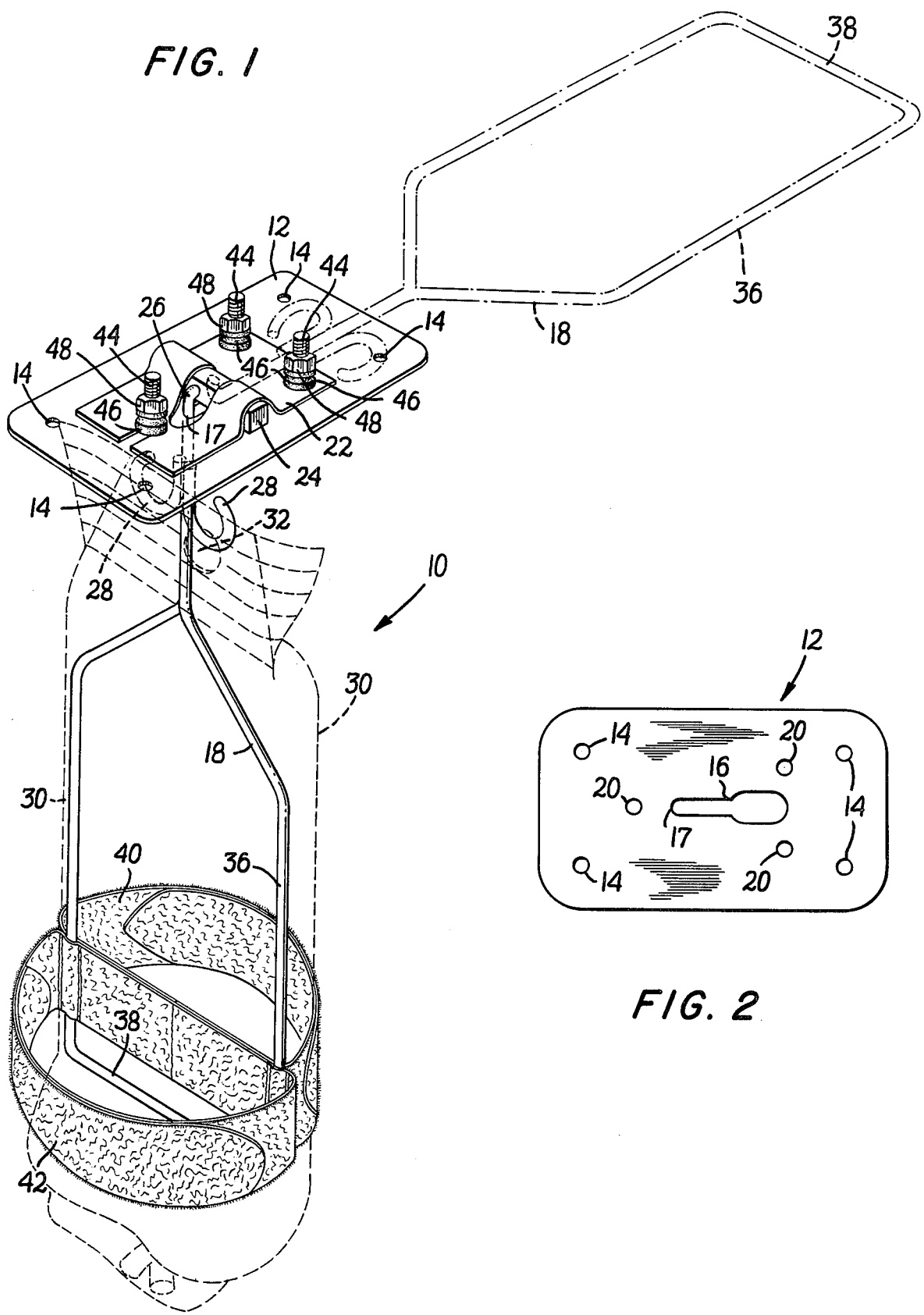

RETRACTABLE PLASMA CONTAINER HOLDER

BACKGROUND OF THE INVENTION

The present invention relates to a retractable holder for pliable plasma or other intravenous fluid containers and, in particular, to a holder adapted to be attached to the ceiling of an ambulance.

Prior to the present invention, ambulances have been equipped with fixed or removable hooks or holders for hanging containers for plasma and other intravenous (I-V) fluids near a patient. Such hooks and holders often provide little restraint against movement of the container, thus affecting the flow rate of the I-V fluid or plasma. In some arrangements there is some risk of the containers falling from the bracket or holder, an obvious hazard to the well-being of the patient. Many of the holders presently used in ambulances are also inconvenient to use, thus taking up valuable and sometimes critical time of the attendant.

SUMMARY OF THE INVENTION

There is provided, according to present invention an improved holder that is designed to be ceiling-mounted (particularly on the ceiling of an ambulance), retractable when not in use and able to hold a rigid or pliable plasma or other intravenous fluid container stationary. The holder has a hanger which holds one or two intravenous containers. A ceiling plate bracket secures the hanger to the ceiling and enables it to be positioned and held parallel to and flush with the ceiling when not in use and to be positioned and held vertically for use. When the hanger is parallel to the ceiling (horizontal), there are no protrusions or obstructions which could injure someone working over a patient in the close quarters of an ambulance. When the plasma container holder is in its vertical position, it is capable of holding two pliable intravenous containers stationary in a moving vehicle. Adjustable straps, preferably of the hook-and-loop cloth type, for example "Velcro" material, provide easy access for changing containers and are affixed to the hanger to hold the containers in place.

The bracket of the holder comprises a ceiling plate having an elongated slot. A support prism is positioned on one side of the ceiling plate with its major axis substantially perpendicular to the length of the slot. A spring clip attached to the plate clamps the support prism with one flat face against the plate while allowing the prism to be rotated around its major axis to another flat face upon the imposition of a substantial force. The hanger is connected to the support prism and extends through the slot in the plate. The hanger is thus held in positions corresponding to the flat faces of the prism two of which are and arranged to position the hanger parallel and normal to the ceiling.

In the preferred form of the holder, the prism and spring clips are recessed in the ceiling on top of the ceiling plate. Only the ceiling plate and hanger then project into the ambulance. Folding the hanger parallel to the ceiling when not in use thus keeps the ambulance free of obstructions. When needed, however, the hanger is merely swung into operative position, a quick operation conserving life-saving moments.

The preferred hook and loop cloth strap for tying the container on the holder also lends itself to quickly setting-up the apparatus. The attendant merely draws the strap about the container to connect it to the holder.

The spring clips and prism hold the hanger in its operative position without the seasick swinging which a careening ambulance gives known, merely suspended containers. The stationary container can provide a more stable flow of fluids vital to the patient. Moreover, the stationary container cannot swing to tug the connected catheter from the patient.

All the described advantages of freeing space in an ambulance but providing quick, stable operation when needed are achieved with a structural simplicity which assures reliable operation. Only the holder and prism rotate on the ceiling plate. There are no extra parts to locate, latches to close, pins to insert or knots to tie for either positioning the holder or keeping it and the container stable.

BRIEF DESCRIPTION OF THE DRAWINGS

For a better understanding of the invention, reference may be made to the following description of an exemplary embodiment taken in conjunction with the accompanying drawings, in which:

FIG. 1 is a perspective view of one embodiment; and

FIG. 2 is a plan view of the ceiling plate in the embodiment.

DESCRIPTION OF THE PREFERRED EMBODIMENT

A holder for a plasma container is designated generally by reference number 10 in FIG. 1. The holder has a bracket comprising a flat plate 12 adapted to be mounted to an ambulance ceiling through mounting holes 14. The ceiling plate has an elongated slot 16 with a narrowed end 17. Fasteners extend through holes 20 (FIG. 2) for holding a spring clip 22 on the plate and over a prism 24 having its major axis perpendicular to the length of the slot.

A hanger 18 for supporting and restraining a container of plasma is attached to prism 24 which is resiliently forced toward the plate by the spring clip. The hanger 18 includes an L-shaped portion 26 that provides an offset between the prism 24 and the major portion of the hanger. A pair of hooks 28 are formed near the L-shaped portion of the hanger for supporting the top of a pliable plasma container 30 (shown in shadow) through a hole 32 formed in the container. The hooks 28 and other portions of the hanger 18 extending below the ceiling plate 12 (parallel arms 36 and connecting bar 38) all lie in a plane so that the entire hanger lies flush with the ceiling plate 12 when the hanger 18 is in its horizontal position and not in use.

A pair of adjustable straps 40, 42 such as Velcro® cloth hook-and-loop straps are joined to the arms 36 near the bar 38. The straps 40, 42 hold the pliable plasma container securely on the hanger. The straps permit quick connection and release of the container and their infinite adjustability ensures that various sizes of containers are securely held.

The spring clip 22, which holds the support prism 24 while allowing a substantial force to rotate it about its major axis, is held to the ceiling plate 12 by suitable fastening means: bolts 44 which extend through the holes 20 in the ceiling plate 12; resilient grommets 46; and nuts 48 which hold the grommets in place. The grommets 46 allow the spring clip 22 to move upward when the support prism 24 is rotated to position the hanger 18 and then resiliently hold another face of the prism against the plate to hold the hanger in the new position. The part of the spring clip which extends about the prism is generally semicircular to accommodate rotation of the prism.

The form of the support prism 24 is chosen to have a flat face on the ceiling plate when the hanger 18 is both parallel and perpendicular to the ceiling plate. For a horizontal ceiling, a support prism may thus have the illustrated rectangular crosssection, although other shapes such as octagonal may also be used. If the ceiling is not horizontal, the shapes of the support prism can be altered to ensure that the hanger 18 is vertical when in use and parallel to the ceiling when not in use with a flat face of the prism on the plate in both positions. By having a flat face of the prism on the plate in each position of the hanger the resilient pressure of the spring clip on the prism stably holds the prism and thus the hanger in the selected position.

The narrowed portion 17 of the slot 16 receives the hanger when it is normal to the plate 12 and has a width chosen to correspond to the width of the portion of the hanger 18 in the slot to provide some further lateral stability of the hanger. The opposite, enlarged end of the slot permits the prism to be inserted through the bracket during assembly before installing the spring clip over it by turning the prism to present its narrow cross-section to the larger end of the slot.

The spring clip 22, the support prism 24, and the nuts and grommets 48, 46 are all positioned on top of the plate 12 to be recessed in the ceiling. Only the plate and holder then project into the ambulance and the holder, like the plate, is parallel to the ceiling when not in use to keep free the space beneath the holder.

To operate the holder when required, an attendant merely pulls the hanger from its horizontal position to its operative, vertical position. The relatively long hanger arms 36, in addition to holding the plasma container, also provide a relatively long lever arm for swinging the hanger to its vertical position. The hanger can thus be easily moved while still providing a substantial force for rotating the prism about its major axis. The spring clip may thus be relatively stiff (thereby requiring the substantial force for rotating the prism) to more positively hold the hanger in both positions without making the holder difficult to use.

Plasma containers are then hooked at the top on hooks 28 and tied in place by pulling a strap 40, 42 around the container. The hanger holds the containers steady because the hanger is held against lateral vibration by the norrowed part 17 of the slot, because the spring clip stiffly urges the prism against the plate, and because the prism is stably positioned with a flat face against the plate.

After use, the hanger is merely pushed to the ceiling. The stiff spring clip and flat face of the support prism then cooperate to hold the hanger out of the way until it is needed again.

I claim:

1. A retractable holder suitable for plasma containers comprising:
   a. a ceiling plate having an elongated slot;
   b. a support prism positioned on one side of the ceiling plate with its major axis substantially perpendicular to the length of the slot;
   c. spring clip means attached to the one side of the ceiling plate and resiliently urging the support prism against the ceiling plate while allowing the prism to be rotated around its major axis upon imposition of a substantial force for holding the prism in positions corresponding to the flat surfaces along the major axis of the prism; and
   d. a hanger connected to the prism and including a portion extending through the slot to the other side of the ceiling plate, this portion of the hanger swinging back and forth along the length of the slot upon rotation of the prism and including means for supporting and restraining at least one container.

2. A holder as set forth in claim 1 in which the container support means comprises at least one hook formed on the hanger.

3. A holder as set forth in claim 1 in which the container support means comprises at least one adjustable strap for supporting a container.

4. A holder as set forth in claim 1 in which the prism is rectangular.

5. A holder as set forth in claim 1 in which the spring clip means includes a generally semicircular portion which embraces the prism and biases it onto the ceiling plate while permitting a substantial force to rotate the prism.

6. A holder as set forth in claim 1 in which the portion of the hanger between the prism and the plate is generally L-shaped so that the hanger is offset from and essentially parallel to the ceiling plate in one position of the prism.

7. A holder as set forth in claim 6 wherein the slot in the ceiling plate includes a narrowed part for capturing the hanger in a position substantially normal to the ceiling plate when the prism is in another position and for holding the hanger against lateral movement when the hanger is substantially normal to the plate.

8. A retractable holder suitable for plasma containers comprising:
   a. a plate mounted over a recess in a ceiling and having an elongated slot with a narrowed portion;
   b. a support prism positioned in the recess on the side of the plate adjacent the ceiling, the major axis of the prism being substantially perpendicular to the length of the slot;
   c. spring clip means positioned in the recess and attached to the plate for resiliently urging the prism against the plate and for allowing the prism to be rotated around the major axis upon imposition of a substantial force for holding the prism in positions corresponding to the flat surfaces along the major axis of the prism; and
   d. a hanger connected to the prism and extending through the slot in the plate, the portion of the hanger extending through the slot including means for supporting and restraining at least one container, the narrowed portion of the slot capturing the hanger in a position substantially normal to the plate when the prism is in one position, the portion of the hanger between the prism and the plate being generally L-shaped so that the hanger is offset from and essentially parallel to the plate and the ceiling when the prism is in another position.

9. A retractable holder suitable for plasma containers comprising:
   a. a ceiling plate having an elongated slot;
   b. a support prism positioned on one side of the ceiling plate with its major axis substantially perpendicular to the length of the slot;
   c. spring clip means attached to the ceiling plate and resiliently urging the support prism against the ceiling plate while allowing the prism to be rotated around its major axis upon imposition of a substantial force for holding the prism in positions corresponding to the flat surfaces along the major axis of the prism;

d. a hanger connected to the prism and including a portion extending through the slot in the ceiling plate, this portion of the hanger including means for supporting and restraining a top of a container and means, infinitely adjustable, for holding a lower part of a container.

10. A holder as set forth in claim 9 wherein the means for supporting and restraining a container comprises a hook on the part of the hanger which projects through the slot in the ceiling plate for supporting and restraining a top of a container.

11. A holder as set forth in claim 9 wherein the hanger further includes an arm extending away from the ceiling plate and the hook on the hanger.

12. A holder as set forth in claim 11 wherein the hook and arm are in a plane.

13. A holder as set forth in claim 11 and further comprising an adjustable hook and loop cloth strap on the arm for holding a lower part of a container.

14. A retractable holder suitable for plasma containers comprising:
a. a ceiling plate having an elongated slot;
b. a support prism positioned on one side of the ceiling plate with its major axis substantially perpendicular to the length of the slot;
c. spring clip means attached to the ceiling plate and resiliently urging the support prism against the ceiling plate while allowing the prism to be rotated around its major axis upon imposition of a substantial force for holding the prism in positions corresponding to the flat surfaces along the major axis of the prism;
d. a hanger conected to the prism and including a portion extending through the slot in the ceiling plate, this portion of the hanger including a pair of hooks for supporting and restraining at least a top of two containers and a pair of parallel arms extending away from the plate and the hooks; and
e. an adjustable hook and loop cloth strap on the parallel arms for holding a lower part of two containers.

* * * * *